United States Patent [19]

Watson

[11] 3,954,890

[45] May 4, 1976

[54] PRODUCTION OF AROMATIC BETA ALCOHOLS

[75] Inventor: James M. Watson, Big Spring, Tex.

[73] Assignee: Cosden Oil & Chemical Company, Big Spring, Tex.

[22] Filed: Mar. 23, 1972

[21] Appl. No.: 237,550

[52] U.S. Cl............... 260/621 H; 260/586 C;
260/612 R; 260/612 D; 260/613 R; 260/613
D; 260/619 D; 260/619 F; 260/623 R;
260/624 R; 260/590 E
[51] Int. Cl.².................. C07C 37/06; C07C 45/00;
C07C 27/00
[58] Field of Search........ 260/621 H, 586 R, 612 R,
260/612 D, 613 R, 613 D, 619 D, 619 F, 623
R, 624 R

[56] References Cited
UNITED STATES PATENTS

| | | | |
|---|---|---|---|
| 2,503,641 | 4/1950 | Taylor et al. | 260/621 H |
| 2,671,808 | 3/1954 | Johnston et al. | 260/586 R |
| 2,773,087 | 12/1956 | Stork | 260/586 R |
| 2,773,099 | 12/1958 | Stork | 260/586 R |

*Primary Examiner*—Norman Morgenstern

[57] ABSTRACT

Condensed ring polycyclic aromatic beta-alcohols are produced by a process which includes initially reacting a cyclic ketone, such as cyclohexanone with a secondary amine to yield an enamine of the cyclic ketone. The enamine is thereafter reacted with an ethylenically unsaturated ketone, such as methyl vinyl ketone, to yield a condensed ring ketone such as octalone which is thereafter dehydrogenated, preferably with a copper chromite catalyst to yield a pure aromatic beta-alcohol such as beta-naphthol.

10 Claims, No Drawings

PRODUCTION OF AROMATIC BETA ALCOHOLS

BACKGROUND OF THE INVENTION

This invention relates to aromatic beta-alcohols. In another aspect, this invention relates to a novel process for the production of pure aromatic beta-alcohols such as beta-naphthol. In another aspect, this invention relates to a novel process for the production of pure beta-naphthol from cyclohexanone and methyl vinyl ketone feed materials.

Aromatic beta alcohols, such as beta-naphthol are used in the production of azo dyes. It is generally required that such aromatic beta-alcohol precursors be very pure and contain little or none of the alpha isomers. For example, beta-naphthol which is generally used as a precursor in the formation of azo dyes, must contain less than 0.05% of alpha-naphthol.

Conventionally, beta-naphthol is produced by a process which involves the initial sulfonation of naphthalene to yield sodium beta-naphthalene sulfonate. The sodium beta-naphthalene sulfonate is then fused with caustic soda to yield a product containing beta-naphthol. The beta-naphthol is recovered from the process in pure form by sublimation, which generally includes distilling the product in vacuum. Thus, this prior art technique utilizes a caustic fusion step which is cumbersome and has the ecological disadvantage of emitting pollutants into the environment. Furthermore, the crude product must be purified by the use of expensive and time-consuming techniques.

Accordingly, one object of this invention is to provide a novel process for the synthesis of aromatic beta-alcohols.

Another object of this invention is to provide a novel process for the production of aromatic beta-alcohols, such as beta-naphthol which does not utilize a caustic fusion step.

A further object of this invention is to provide a novel process which will produce high yields of very pure beta-naphthol which is suitable for use in the production of azo dyes.

According to the invention, fused ring polycyclic aromatic beta-alcohols are produced by a process which comprises initially reacting cyclohexanone or a similar such compound with a secondary amine to thereby form an enamine thereof. The enamine is then reacted with an ethylenically unsaturated ketone having an aliphatic backbone with at least 4 carbon atoms, which results in cycloacylation of the enamine. The cycloacylated product is then dehydrogenated to yield a fused ring polycyclic aromatic beta-alcohol.

According to a preferred embodiment of this invention, cyclohexanone is initially reacted with a secondary amine to form an enamine which is in turn reacted with methyl vinyl ketone to yield an octalone mixture. The octalone mixture is thereafter dehydrogenated with a catalyst such as copper chromite to yield pure beta-naphthol.

The cyclic ketone feed materials which can be used within the scope of this invention include cyclohexanone and condensed 6-membered ring compounds, such as tetralones and decalones, as well as the cyclic, acylic and halogen substituted derivatives thereof. Suitable cyclic ketone feed materials which can be used in accordance with this invention have structural formulas of:

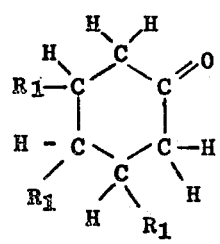 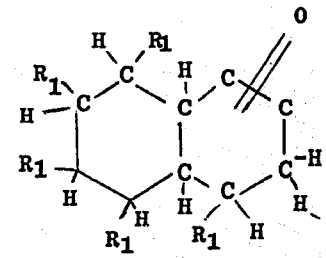 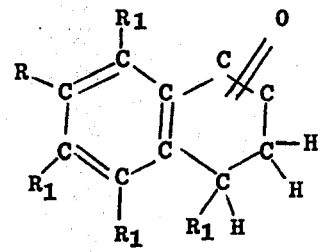

I.  II.  III.

wherein $R_1$ is selected from hydrogen, halogen, and the following radicals having from 1 to about 10 carbon atoms; alkyl, alkenyl, alkynl, cycloalkyl, cycloalkenyl, aryl, aralkyl, and alkoxy. Examples of suitable such preferred materials which can be used in the scope of this invention include cyclohexanone; 2-decalone, 2-tetralone; 1-tetralone; 1-decalone, and the like. The preferred cyclic ketone feed materials which are used in the scope of this invention are materials having structural formula I above. The most preferred cyclic ketone feed material which is used in the scope of this invention is cyclohexanone. Cylohexanone is conveniently derived from the air oxidation of cyclohexane in the presence of a cobalt naphthanate catalyst, for example.

The cyclic ketone is reacted initially with the secondary amine to form an enamine thereof as illustrated below:

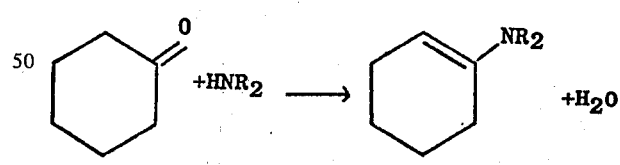

wherein $HNR_2$ is a secondary amine which will form an enamine with a cyclohexanone ring. Examples of suitable such secondary amines are morpholine, pyrrolidine, hexamethylene imine, methylaniline, camphidine, diethylamine, piparidine, and the like. The preferred secondary amines are the cyclic amines, such as morpholine and pyrrolidine.

Generally from about 1.3 to about 3 moles of the secondary amine are admixed with each mole of the cyclic ketone, and preferably about one and one-half moles of amine per mole of ketone. The reaction is carried out at a temperature in the range of from about 75°C to about 120°C under conditions whereby the by-product water is removed from the reaction zone as it is formed. The reaction can be carried out under any convenient pressure, either atmospheric or above or below atmospheric.

The reaction between the secondary amine and the cyclic ketone occurs preferably within a solvent for these materials and preferably within a solvent which is insoluble or only slightly soluble in water and which azeotropes with by-product water which is formed in the reaction. The preferred reaction procedure is to conduct the reaction in a solvent which forms an azeotrope with water and to maintain the reaction at the boiling point of the mixture. In this manner, the azeotrope formed between the solvent and water can be collected, the water removed therefrom, and solvent returned to the reaction zone. Suitable such solvents for the reaction generally include the aromatic solvents, such as benzene, toluene and xylene. The reaction should proceed for a sufficient time to complete the formation of the enamine. The reaction is generally complete in about 1 to 10 hours.

The enamine intermediate product is thereafter reacted with an ethylenically unsaturated ketone to yield a condensed ring polycyclic hydrocarbon with a keto radical in the beta position. Thus, it is necessary that the ketone have an aliphatic backbone of at least 4 carbon atoms and the vinylene (—CH=CH—) and carbonyl

radicals be at adjacent positions in the backbone of the molecule. Suitable such ketones have a general structural formula:

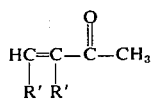    IV.

wherein R' is selected from hydrogen and alkyl, aryl, and aralkyl groups having from 1 to about 10 carbon atoms. The preferred ethylenically unsaturated ketones used in the scope of this invention are the vinyl ketones and the most preferred reactant material is methyl vinyl ketone. Methyl vinyl ketone feed material is conveniently derived from acetylene via dimerization and subsequent hydration of the dimer.

The mole-ratio between the ethylenically unsaturated ketone and the enamine can generally be in the range of from 0.8:1 to 1.2:1. Preferably, equal molar amounts of these materials are admixed in the reaction zone.

The reaction between the enamine and the ethylenically unsaturated ketone generally occurs in a solvent for the materials and at a temperature between 75°C and 120°C. Preferably, the reaction mixture is heated at reflux from about 0.5 to about 3 hours. The reaction generally is carried out at autogenous pressures. After the cycloacylation of the enamine compound with the ethylenically unsaturated ketone, the secondary amine compound is split therefrom preferably by the use of an acid or base in the following manner:

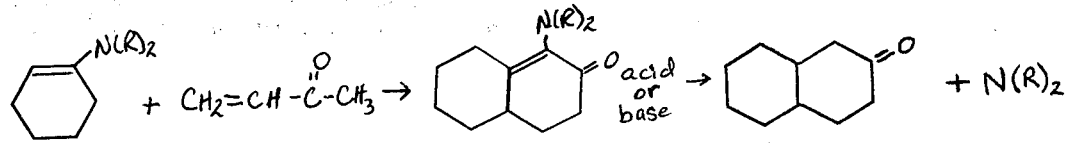

Any suitable acid or base which is nondeleterious to the reaction can be used for example, hydrochloric acid, sulfuric acid, phosphoric acid, sodium hydroxide, potassium hydroxide, ammonium hydroxide, and the like. Generally from about 0.5 to 1.0 moles of acid or base is used for each mole of the cycloacylated reaction product. The acid or base is used in aqueous solution.

The product of the reaction between the ethylenically unsaturated ketone and the enamine generally comprises a beta-ketone of a hydrocarbon comprising condensed 6-membered rings. This reaction product is then dehydrogenated to yield a polycyclic aromatic beta-alcohol. Polycyclic aromatic beta-alcohols which can be produced in accordance with the subject invention have the general structural formula of:

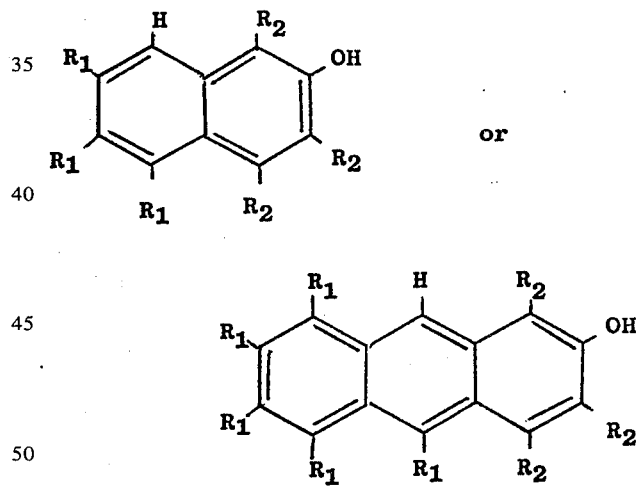

wherein $R_1$ is selected from hydrogen, halogen and the following organic radicals having from 1 to about 10 carbon atoms: alkyl, alkenyl, alkynl, cycloalkyl, cycloalkenyl, aryl, aralkyl, and alkoxy; and $R_2$ is selected from hydrogen and alkyl, aryl and aralkyl having from 1 to about 10 carbon atoms. With respect to the tricyclic compounds, they may be anthracenic or phenanthrenic in structure.

Generally, any dehydrogenation catalyst which will not deleteriously affect the reaction can be used in the scope of this invention. Based upon product selectivity and yield, the preferred catalyst to be used in the scope of this invention is copper chromite. The dehydrogenation can occur in liquid phase by admixing the reaction product with copper chromite at a temperature of between about 250° and 350°C. If desired, the dehydrogenation can occur in the presence of a suitable diluent.

Other suitable dehydrogenation catalysts which can be used in the scope of this invention include: platinum or palladium, on alumina, nickel, etc.

The following example is given to better facilitate the understanding of this invention and is not intended to limit the scope thereof:

EXAMPLE

Morpholine enamine of cyclohexanone was produced by initially admixing 360 parts by weight of morpholine with 195 parts by weight of cyclohexanone in 265 parts by weight of benzene in a reactor fitted with a reflux condenser and a Dean-Stark trap between the condenser and the reactor. The reaction mixture was heated at reflux (80°C) until the cessation of water collection in the trap. Approximately 41 parts by weight of water was collected in the trap during a 7 hour reflux period. The resulting reactant mixture was fractionated to obtain 316 parts by weight of the morpholine enamine of cyclohexanone which was a 95.4% yield.

Next, the 46 parts by weight of the morpholine enamine of cyclohexanone was admixed with 19 parts by weight of methyl vinyl ketone in 53 parts by weight of benzene solvent and heated at reflux (80°C) for 3 hours. After the 3 hour period, the reaction mixture was cooled and treated with the solution comprising 40 parts by weight of methanol, 25 parts by weight of water and 5 parts by weight of sodium hydroxide to yield a resulting mixture which was then heated at reflux (70°C) for 2 hours and thereafter diluted with approximately 100 parts by weight of water and separated in the 2-phases. The aqueous phase was extracted with ether to yield a phase which was combined with the organic phase and thereafter distilled to obtain a product having a boiling point of from 93°–117°F at 3 millimeters Hg. The product yield comprised 73.5% (based on octalones). A gas liquid chromatographic analysis of this product showed it to include 81.6% octalone, an 8.6 mole % decalone, and 10% other cyclic materials. The resulting mixture was then agitated with 10% of its weight of copper chromite and maintained at a temperature of 250°–350°c for 4 hours to obtain a 75% yield of pure beta-naphthol.

It is to be understood that various modifications of this invention will now be apparent to one skilled in the art upon reading this specification and it is intended to cover such modifications as fall within the scope of the appended claims.

What is claimed is:

1. A process of producing a condensed ring polycyclic aromatic beta alcohol comprising:
    a. reacting a first compound having a structural formula selected from:

wherein $R_1$ is selected from hydrogen, halogen and the following radicals having from 1 to about 10 carbon atoms: alkyl, alkenyl, alkynl, cycloalkyl, cycloalkenyl, aryl, aralkyl and alkoxy; with a secondary amine which will form an enamine with a cyclohexanone ring, under anhydrous conditions, and at a temperature in the range of from about 75°C to about 120°C to thereby form an enamine of said first compound;
    b. forming a cycloacylated compound by contacting said enamine with a second compound having the structural formula of:

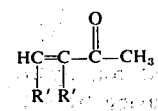

wherein $R'$ is selected from hydrogen and alkyl, aryl, and aralkyl groups having from 1 to about 10 carbon atoms, said contacting occurring by admixing from 0.8 to 1.2 moles of said second compound with each mole of said enamine at a temperature between about 75°C and about 120°C thereby forming a reaction product between said enamine and said second compound and thereafter contacting from about 0.5 to 1 mole of acid or base with each mole of the reaction product of said enamine and said second compound to remove said secondary amine therefrom and form said cycloacylated product;
    c. recovering said cycloacylated product; and
    d. dehydrogenating said cycloacylated product to yield said condensed ring polycyclic aromatic beta alcohol.

2. The process of claim 1 wherein said enamine is formed by contacting said first compound and said secondary amine in a solvent therefor in a reaction zone and heating the materials to a temperature in the range of from about 75°C to about 120°C and removing by-product water from the reaction zone as it is formed.

3. The process of claim 2 wherein said secondary amine is a cyclic amine.

4. The process of claim 3 wherein said cyclic amine is selected from morpholine and pyrrolidine.

5. The process of claim 4 wherein said dehydrogenation occurs by contacting said cycloacylated product with a copper chromite catalyst at a temperature of between about 250°C and 350°C.

I.

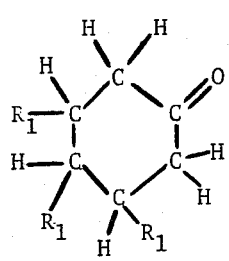

II.

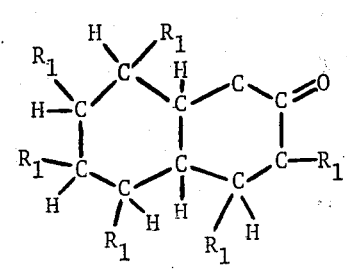

III.

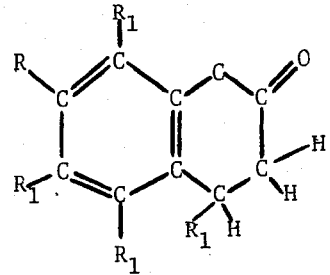

6. A process for producing a beta naphthol comprising:

a. contacting a first compound having a structural formula of:

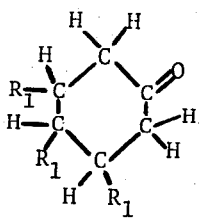

wherein $R_1$ is selected from hydrogen, halogen and the following radicals having from 1 to about 10 carbon atoms: alkyl, alkenyl, alkynl, cycloalkyl, cycloalkenyl, aryl, aralkyl, and alkoxy, with a secondary amine which will form an enamine with a cyclohexanone ring, in a solvent therefor, and heating the material to a temperature in the range of from about 75°C to about 120°C and removing by-product water from the reaction zone as it is formed to thereby form an enamine of said first compound;

b. forming an octalone therefrom by contacting said enamine with a second compound having the structural formula of:

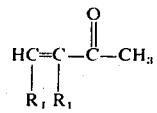

wherein $R_1$ is selected from hydrogen and alkyl, aryl, and aralkyl groups having from 1 to about 10 carbon atoms in a solvent therefor and at a temperature between about 75°C and about 120°C with the mole ratio of said second compound to said enamine being in the range of from 0.8:1 to 1.2:1 to form a reaction product between said enamine and said second compound, and thereafter contacting from about 0.5 to about 1 mole of acid or base with each mole of the reaction product of said enamine and said second compound to thereby remove said secondary amine therefrom and form said octalone;

c. recovering said octalone; and d. dehydrogenating said octalone to form said beta-naphthol.

7. The process of claim 6 wherein said secondary amine is a cyclic amine.

8. The process of claim 7 wherein said cyclic amine is selected from morpholine and pyrrolidine.

9. The process of claim 8 wherein said first compound is cyclohexanone and said second compound is methyl vinyl ketone.

10. The process of claim 8 wherein said dehydrogenation occurs by contacting said octalone with a copper chromite catalyst at a temperature of between about 250°C and 350°C.

* * * * *